(12) United States Patent
Im et al.

(10) Patent No.: US 11,464,864 B2
(45) Date of Patent: Oct. 11, 2022

(54) DRUG-BOUND COMPOUND AND USE THEREOF

(71) Applicant: SOONCHUNHYANG UNIVERSITY INDUSTRY ACADEMY COOPERATION FOUNDATION, Asan-si (KR)

(72) Inventors: Jungkyun Im, Asan-si (KR); Tarun Kumar Pal, Bangalore (IN)

(73) Assignee: SOONCHUNHYANG UNIVERSITY INDUSTRY ACADEMY COOPERATION FOUNDATION, Asan-si (KR)

( * ) Notice: Subject to any disclaimer, the term of this patent is extended or adjusted under 35 U.S.C. 154(b) by 169 days.

(21) Appl. No.: 16/677,212

(22) Filed: Nov. 7, 2019

(65) Prior Publication Data

US 2020/0147227 A1 May 14, 2020

(30) Foreign Application Priority Data

Nov. 8, 2018 (KR) .......................... 10-2018-0136400

(51) Int. Cl.
*A61P 35/00* (2006.01)
*A61K 47/54* (2017.01)
*A61K 31/4745* (2006.01)

(52) U.S. Cl.
CPC ........ *A61K 47/549* (2017.08); *A61K 31/4745* (2013.01); *A61P 35/00* (2018.01)

(58) Field of Classification Search
CPC .............................. A61K 47/549; A61P 35/00
See application file for complete search history.

(56) References Cited

PUBLICATIONS

Pinded et al. (2000).*
McMahon et al. (2000).*

* cited by examiner

*Primary Examiner* — Paul V Ward
(74) *Attorney, Agent, or Firm* — Sughrue Mion, PLLC

(57) ABSTRACT

The present invention relates to a CPT-bound compound or a pharmaceutically acceptable salt thereof, the CPT-bound compound being obtained by binding CPT (or a CPT derivative) and guanidine to a reduced monosaccharide. The CPT-bound compound enhances solubility and cell permeability of the CPT drug, which makes it possible to effectively deliver CPT to target cells. Therefore, a pharmaceutical composition comprising, as an active ingredient, the CPT-bound compound or a pharmaceutically acceptable salt thereof is expected to be able to effectively treat cancer, in particular, colorectal cancer, even with a low dose of CPT.

11 Claims, 5 Drawing Sheets

DRUG-BOUND COMPOUND AND USE THEREOF

CROSS REFERENCE

This application claims priority to and the benefit of Korean Patent Application No. 10-2018-0136400, filed Nov. 8, 2018, the disclosure of which is incorporated herein by reference in their entirety.

TECHNICAL FIELD

The present invention relates to a drug-bound compound and a use thereof, and more particularly, to a camptothecin (CPT)-bound compound, obtained by binding a CPT drug and guanidine to a monosaccharide to enhance cell permeability of CPT, and a use thereof.

BACKGROUND ART

Camptothecin (CPT) is an alkaloid extracted from the Camptotheca acuminata tree and is known as a potent antitumor and antibiotic substance that acts through inhibition of DNA topoisomerase I (TOPO I). However, despite such effects, CPT had limitations in formulation preparation and application as cancer therapeutic agents due to low solubility, reversible hydrolytic nature, and the like.

In order to overcome the above limitations, various CPT derivatives, such as irinotecan and topotecan, with improved properties of CPT have been developed. However, it is also difficult to deriver derivatives effectively due to low cell permeability and the like.

Also, as drug delivery systems for overcoming the limitations of the above-mentioned CPT or CPT derivatives, various methods for delivery of CPT such as a liposome capsule containing camptothecin (Korea Patent No. 10-0711315) and a conjugate obtained by binding a cell penetrating peptide (CPP) to camptothecin (Korea Patent No. 10-1394768) have been proposed.

However, to date, none of the proposed CPT delivery methods has shown a sufficient clinical therapeutic effect. Accordingly, there is a need for development of a drug delivery technique which can effectively deliver CPT while having enhanced stability and efficacy.

DISCLOSURE OF INVENTION

Technical Problem

The present inventors have developed a CPT-bound compound in order to solve problems such as low solubility and decreased cell permeability of CPT. Specifically, an object of the present invention is to provide a CPT-bound compound, obtained by binding CPT or a CPT derivative, and guanidine to a monosaccharide, and a pharmaceutical composition comprising same.

Solution to Problem

In order to achieve the above object, an embodiment provides a CPT-bound compound or a pharmaceutically acceptable salt thereof, the CPT-bound compound being obtained by binding CPT or a CPT derivative, and guanidine to a reduced monosaccharide.

In addition, an embodiment provides a pharmaceutical composition for treating cancer, comprising, as an active ingredient, the CPT-bound compound or a pharmaceutically acceptable salt thereof.

Advantageous Effects of Invention

According to the embodiments, a CPT-bound compound or a pharmaceutically acceptable salt thereof is obtained by binding CPT (or a CPT derivative) and guanidine to a reduced monosaccharide. The CPT-bound compound enhances solubility and cell permeability of a CPT drug, which makes it possible to effectively deliver CPT to target cells. Therefore, a pharmaceutical composition comprising, as an active ingredient, the CPT-bound compound or a pharmaceutically acceptable salt thereof is expected to be able to effectively treat cancer, in particular, colorectal cancer, even with a low dose of CPT.

BEST MODE FOR CARRYING OUT THE INVENTION

Figure 1:
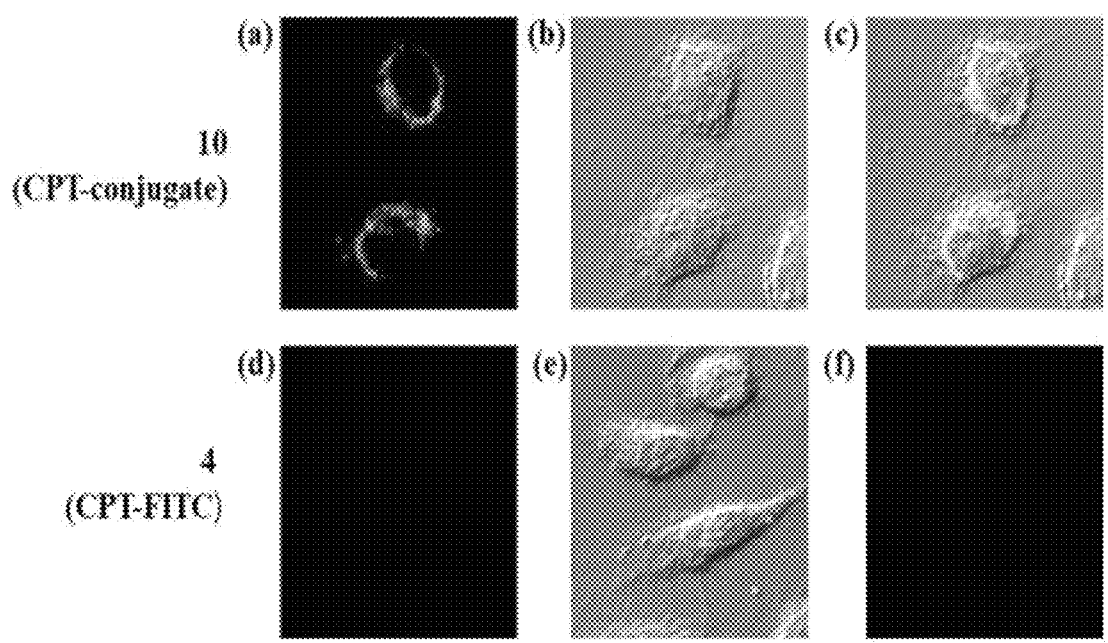
FIG. 1 illustrates results obtained by comparing the cell uptake effect of a CPT-bound compound according to an embodiment with that of CPT alone. Here, (a) and (d) represent fluorescent images, (b) and (e) represent DIC images, and (c) and (f) represent images obtained by merging the fluorescent images with the DIC images.

In an aspect of the present invention, there is provided a CPT-bound compound or or a pharmaceutically acceptable salt thereof, the CPT-bound compound being obtained by binding CPT or a CPT derivative, and guanidine to a reduced monosaccharide.

As used herein, the term "binding" refers to a covalent, ionic, or hydrophobic interaction that allows molecules to be united so as to mainitain proximity. Specifically, the binding is preferably a covalent link.

In an embodiment of the present invention, the monosaccharide may be any one selected from the group consisting of glucose, sorbitol, fructose, mannose, galactose, and ribose, and the reduced monosaccharide may be preferably sorbitol.

In an embodiment of the present invention, the CPT derivative may be, but is not limited to, one or more selected from the group consisting of topotecan, irinotecan, silatecan, cositecan, exatecan, lurtotecan, gimatecan, belotecan, and rubitecan.

In an embodiment of the present invention, the CPT or the CPT derivative may be bound via a linker. The linker may have the following formula, but is not limited thereto:

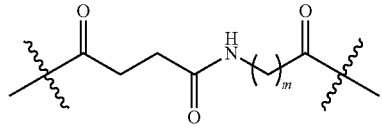

Wherein, m may be an integer of 3 to 8, and m may be preferably an integer of 5.

In an embodiment of the present invention, the guanidine may be bound via a linker. The linker may have the following formula, but is not limited thereto:

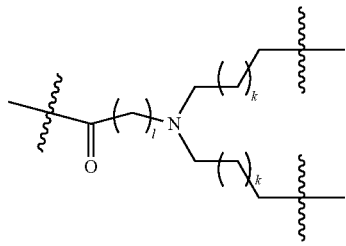

Wherein, l and k may each be an integer of 3 to 8, and l and k may each be preferably an integer of 5.

In an embodiment of the present invention, the CPT-bound compound or a pharmaceutically acceptable salt thereof may be represented by the following Formula 1.

[Formula 1]

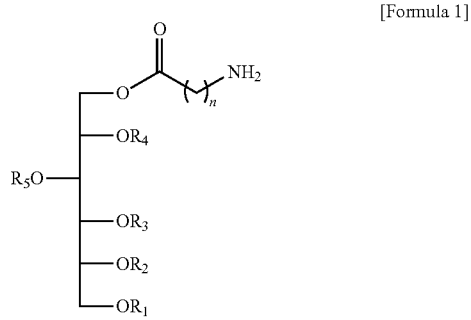

In the formula, $R_1$ is represented by the following Formula 2,

[Formula 2]

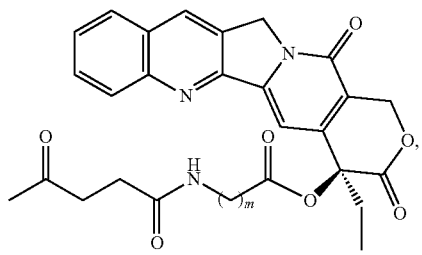

and $R_2$ to $R_5$ are represented by the following Formula 3,

[Formula 3]

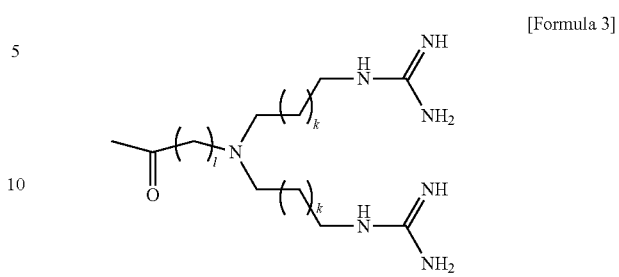

in the above formulae, n, m, l, and k may each be an integer of 3 to 8, and n, m, l and k may each be preferably an integer of 5.

In Formula 1, in a case where $R_1$ is represented by the Formula 2, $R_2$ to $R_5$ may be represented by Formula 3.

In addition, in Formula 1, $R_1$ to $R_5$ may be represented by the Formula 2 or the Formula 3. Here, one or more of $R_1$ to $R_5$ may be represented by Formula 3, or three or more thereof may be represented by Formula 3.

In an embodiment of the present invention, the CPT-bound compound may be 1-O-[20-O—(N-succinyl-6-aminohexanoyl)camptothecin]-2,3,4,5-tetra-O—(N-{bis-[3-(N',N''-bis-(tert-butoxycarbonyl)-guanidino)-propyl]}-6-aminohexanoyl)-6-O-(6-aminohexanoyl)-D-sorbitol.

In an embodiment of the present invention, the pharmaceutically acceptable salt of the CPT-bound compound may be in the form of an acid addition salt formed with an inorganic acid or an organic acid. The inorganic acid may be any one selected from the group consisting of hydrochloric acid, sulfuric acid, phosphoric acid, nitric acid, and hydrobromic acid. The organic acid may be any one selected from the group consisting of acetic acid, trifluoroacetic acid, lactic acid, pyruvic acid, malonic acid, succinic acid, glutaric acid, fumaric acid, tartaric acid, maleic acid, citric acid, benzoic acid, ascorbic acid, methanesulfonic acid, ethanesulfonic acid, 2-hydroxyethanesulfonic acid, and camphoric acid.

Preferably, the pharmaceutically acceptable salt of the CPT-bound compound may be in the form of an acid addition salt formed with hydrochloric acid.

In an embodiment of the present invention, the pharmaceutically acceptable salt of the CPT-bound compound may be 1-O-[20-O—(N-succinyl-6-aminohexanoyl)camptothecin]-2,3,4,5-tetra-O—(N-{bis-[3-(N',N''-bis-(tert-butoxycarbonyl)-guanidino)-propyl]}-6-aminohexanoyl)-6-O-(6-aminohexanoyl)-D-sorbitol•8HCl; or 1-O-[20-O—(N-succinyl-6-aminohexanoyl)camptothecin]-2,3,4,5-tetra-O—(N-{bis-[3-(N',N''-bis-(tert-butoxycarbonyl)-guanidino)-propyl]}-6-aminohexanoyl)-6-O-(6-aminohexanoyl)-D-sorbitol•9HCl.

In an embodiment of the present invention, the CPT-bound compound or a pharmaceutically acceptable salt thereof may take the form of enantiomer, diastereomer, or a mixture thereof.

In addition, in another aspect of the present invention, there is provided a pharmaceutical composition for treating cancer, comprising, as an active ingredient, the CPT-bound compound or a pharmaceutically acceptable salt thereof.

In an embodiment of the present invention, the cancer may be one or more selected from colorectal cancer, lung cancer, pancreatic cancer, ovarian cancer, breast cancer, prostate cancer, liver cancer, head and neck cancer, gastric cancer, bladder cancer, non-Hodgkin's lymphoma, melanoma, leukemia, neuroblastoma, and glioblastoma.

The pharmaceutical composition is suitable for treating various cancers under various conditions. From this point of view, the term "treatment" as used herein includes both therapeutic and prophylactic meanings. Thus, the pharmaceutical composition can be used at the early stages of cancer, or even after cancer has progressed significantly, including metastasis. In particular, the term "treatment" means decreased rate of cancer cell proliferation, destruction of cancer cells, decreased mass or size of cancer, decreased cancer metastasis, delayed progression of cancer and complete inhibition of cancer, enhanced survival, or any other appropriate clinical endpoint.

The pharmaceutical composition may be administered intravascularly, with preferably being administered intravenously. A medicinal preparation form of the pharmaceutical composition is preferably a lyophilized preparation, and may be an injection preparation which can be diluted to prepare an injection solution at the time of use, a dilute solution preparaton which can be administered as it is, or the like.

The pharmaceutical composition is preferably a lyophilized preparation in consideration of chemical stability of CPT and formation stability of the CPT-bound compound.

In a case where the pharmaceutical composition is administered, water, physiological saline, 5% glucose or mannitol aqueous solution, water-soluble organic solvent (for example, single solvents such as glycerol, ethanol, dimethylsulfoxide, N-methylpyrrolidone, polyethylene glycol, and Cremophor, or mixed solvents thereof), and the like may be commonly used so that the pharmaceutical composition is used as a solution of the medical preparation.

The medicinal preparation may contain a commonly used pharmaceutically acceptable additive. As the additive, a binder, a lubricant, a disintegrant, a solvent, an excipient, a solubilizer, a dispersant, a stabilizer, a suspending agent, a preservative, a pain-relieving agent, a pigment, a flavoring agent, and the like may be used.

In a case of the lyophilized preparation, the CPT-bound compound may be made into an aqueous solution together with any additives. Subsequently, a pH of the aqueous solution may be adjusted and filter sterilization may be performed. Then, the resultant may be divided and placed in containers, which may, in turn, be lyophilized to prepare a lyophilized preparation. Here, the pH may be adjusted using a pH adjuster or the pH adjustment may be performed with the active ingredient itself.

In a case of the injection preparation, the CPT-bound compound may be made into an aqueous solution together with any saccharide additives. Subsequently, a pH of the aqueous solution may be adjusted and filter sterilization may be performed. Then, the resultant may be divided and placed in containers, to prepare a injection preparation. The pH may be adjusted using a pH adjuster or the pH adjustment may be performed with the active ingredient itself.

A dose of the pharmaceutical composition may vary depending on the patient's sex, age, physiological condition, severity of disease, and the like, and the pharmaceutical composition may be parenterally administered in an amount of, usually 0.01 mg/m$^2$ (body surface area) to 500 mg/m$^2$, and preferably 0.1 mg/m$^2$ to 250 mg/m$^2$, per day for an dult. Administration by injection may be carried out at vein, artery, affected part (tumor part), or the like.

MODE FOR THE INVENTION

Hereinafter, the present invention will be described in more detail by way of the following examples. However, the following examples are only for illustrating the present invention, and the scope of the present invention is not limited thereto.

PREPARATION EXAMPLES

Materials and Methods

S-(+)-Camptothecin, fluorescein-5-isothiocyanate (FITC-I), triethylamine (Et$_3$N), 1-ethyl-3-(3-dimethylaminopropyl) carbodiimide (EDC), 4-dimethylaminopyridine (DMAP), diisopropylethylamine (DIPEA), and trifluoroacetic acid (TFA) were purchased from Sigma-Aldrich Korea Ltd. All solvents were purified and dried by standard methods before use. NMR structure analysis was performed using a Bruker ASPECT 300 instrument at 300 MHz for $^1$H NMR and at 75 MHz for $^{13}$C NMR. For $^1$H NMR, chemical shifts were recorded in parts per million (ppm) for tetramethylsilane (TMS) or deuterium oxide (D$_2$O) used as an internal standard. Mass spectra were obtained using fast atom bombardment (FAB). Analysis results of MALDI-TOF data for high molecular weight compounds were obtained on a Micromass M@DI at the Biomolecular Diversity Core Facility (POSTECH). Medium pressure liquid chromatography (MPLC) was performed with CombiFlash RF+ Lumen UV having Fluka 100 C8-reversed phase silica gel. Analytical RP-HPLC and preparative RP-HPLC were performed with Agilent 1220 Infinity LC Chemstation.

Preparation Example 1

20-O—[N-(tert-butoxycarbonyl)-6-aminohexanoyl] camptothecin (1)

To a solution of (S)-(+)-camptothecin (40 mg, 0.11 mmol) in anhydrous DMF, 6-tert-butoxycarbonyl-aminohexanoic acid (51 mg, 0.22 mmol), EDC (46 mg, 0.24 mmol), and DMAP (7 mg, 0.055 mmol) were added at room temperature under argon atmosphere, and stirring was performed overnight. The reaction mixture was diluted with water (20 ml) and then extracted three times with ethyl acetate (20 ml). The extract was washed successively using 0.1 M hydrochloric acid (30 ml) and distilled water (30 ml). The organic phase was dried over anhydrous Na$_2$SO$_4$ and concentrated in vacuo. The crude residue was purified by SiO$_2$ column chromatography (CH$_2$Cl$_2$:MeOH=25:1), to give the title compound (1) (63 mg, 98%) as a light yellow solid.

mp 154° C., R$_f$0.38 (CH$_2$Cl$_2$:MeOH=20:1); $^1$H NMR (CDCl$_3$): δ 0.91 (t, J=7.4 Hz, 3H), 1.38-1.49 (m, 13H), 1.64-1.68 (m, 2H), 2.10-2.36 (m, 2H), 2.49 (td, J=2.5, 7.3 Hz, 2H), 3.04-3.08 (m, 2H), 4.75 (br s, 1H, NH), 5.26 (s, 2H), 5.39 (d, J=17.2 Hz, 1H), 5.65 (d, J=17.2 Hz), 7.22 (s, 1H), 7.65-7.68 (m, 1H), 7.80-7.83 (m, 1H), 7.92 (d, J=8.1 Hz, 1H), 8.20 (d, J=8.4 Hz, 1H), 8.39 (s, 1H); $^{13}$C NMR (CDCl$_3$): δ 7.7, 24.4, 26.2, 28.5, 29.8, 31.9, 33.8, 40.4, 50.1, 67.2, 75.9, 96.3, 120.5, 128.2, 128.3, 128.4, 12.5, 130.9, 131.6, 146.1, 146.2, 148.8, 152.4, 156.1, 157.6, 167.7, 172.7; MS (FAB) m/z calcd. for C$_{31}$H$_{36}$N$_3$O$_7$ 562.25, found 562.37 [M+H]$^+$.

Preparation Example 2

20-O-(6-aminohexanoyl)camptothecin trifluoroacetic acid salt (2)

A solution of the compound (1) prepared in Preparation Example 1 (61 mg, 0.108 mmol) in 20% TFA-CH$_2$Cl$_2$ (2 ml)

was stirred at room temperature for 1 hour. After evaporation of the solution under reduced pressure, the residue was triturated with diethyl ether (20 ml). The solid obtained was filtered, washed with $CH_2Cl_2$ (20 ml), and then dried in vacuo, to give a TFA salt (49 mg, 79%) of the title compound (2) that did not require further purification.

mp 214° C., $^1$H NMR ($CD_3OD$): δ 1.04 (t, J=7.4 Hz, 3H), 1.42-1.52 (m, 2H), 1.62-1.78 (m, 4H), 2.14-2.28 (m, 2H), 2.59-2.65 (m, 2H), 2.90 (t, J=7.6 Hz, 2H), 5.32 (s, 2H), 5.47 (d, J=16.8 Hz, 1H), 5.61 (d, J=16.8 Hz), 7.36 (s, 1H), 7.68-7.74 (m, 1H), 7.85-7.90 (m, 1H), 8.07 (d, J=8.2 Hz, 1H), 8.16 (d, J=8.5 Hz, 1H), 8.64 (s, 1H); $^{13}$C NMR ($CD_3OD$): δ 8.0, 25.1, 26.6, 28.2, 32.0, 34.2, 40.5, 51.4, 67.7, 77.5, 97.7, 120.5, 129.1, 129.6, 129.8, 130.7, 131.9, 133.3, 147.4, 148.4, 149.4, 153.3, 158.9, 169.6, 173.8; MS (FAB) m/z calcd. for $C_{26}H_{28}N_3O_5$ 462.20, found 462.36 $[M+H]^+$.

Preparation Example 3

20-O—(N-succinyl-6-aminohexanoyl)camptothecin (3)

To a solution of the compound (2) prepared in Preparation Example 2 (30 mg, 0.052 mmol) in anhydrous DMF (2 ml), succinic anhydride (7.8 mg, 0.078 mmol), DMAP (3.1 mg, 0.026 mmol), and pyridine (12.7 ml, 0.156 mmol) were added. The solution was stirred at room temperature under argon atmosphere for 12 hours. The reaction mixture was diluted with distilled water (20 ml) and then extracted three times with ethyl acetate (20 ml). The extract was washed successively using 0.1 M hydrochloric acid (30 ml) and distilled water (30 ml). The organic layer was dried over anhydrous $Na_2SO_4$ and concentrated in vacuo. The crude residue was purified by $SiO_2$ column chromatography ($CH_2Cl_2$:MeOH=10:1), to give the title compound (3) (28 mg, 95%) as a light yellow solid.

mp 162° C., $R_f$ 0.36 ($CH_2Cl_2$:MeOH=10:1); $^1$H NMR ($CDCl_3+CD_3OD$): δ 1.0 (t, J=7.5 Hz, 3H), 1.38-1.54 (m, 4H), 1.62-1.71 (m, 2H), 2.11-2.28 (m, 2H), 2.37-2.59 (m, 6H), 3.13 (t, J=6.3 Hz, 2H), 5.31 (s, 2H), 5.40 (d, J=17.1 Hz, 1H), 5.63 (d, J=17.1, 1H), 7.33 (s, 1H), 7.66-7.71 (m, 1H), 7.82-7.87 (m, 1H), 7.99-8.01 (m, 1H), 8.15-8.18 (m, 1H), 8.54 (s, 1H); $^{13}$C NMR ($d_6$-DMSO): δ 7.5, 24.1, 25.7, 28.7, 30.2, 31.8, 32.2, 33.1, 38.1, 50.2, 75.6, 94.6, 118.8, 127.7, 128.5, 128.9, 129.7, 130.4, 131.6, 145.4, 146.0, 147.8, 152.2, 152.3, 156.5, 162.3, 167.2, 171.9, 172.0; MS (FAB) m/z calcd. for $C_{30}H_{32}N_3O_8$ 562.22, found 562.37 $[M+H]^+$.

Preparation Example 4

20-O-[6-(fluoresceinyl-5-thioureido)-hexanoyl) camptothecin (4)

To a solution of the compound (3) prepared in Preparation Example 3 (15.6 mg, 0.027 mmol) in DMF (1 ml), $Et_3N$ (0.17 ml, 0.90 mmol) and FITC-I (17.60 mg, 0.041 mmol) were added. After performing stirring for 12 h in the dark, the reaction mixture was azeotroped with toluene at 45° C. The concentrated solution was purified by $SiO_2$ column chromatography and preparative TLC was performed, to give the title compound (4) (19 mg, 84%) as a sticky yellow oil.

$R_f$ 0.42 ($CH_2Cl_2$:MeOH=10:1+AcOH (0.1%)); 1H NMR ($CDCl_3$+MeOD): δ 0.88 (t, J=6.6 Hz, 3H), 1.15-1.92 (m, 6H), 2.05-2.38 (m, 2H), 2.39-2.63 (m, 2H), 3.51-3.60 (m, 2H), 5.30 (s, 2H), 5.53 (dd, J=60, 17.1 Hz, 2H), 6.43-6.84 (m, 6H), 7.10 (d, J=9 Hz, 1H), 7.27 (s, 1H), 7.70 (t, J=7.2 Hz, 1H), 7.83 (t, J=7.2 Hz, 1H), 7.85 (s, 2H), 7.86-8.00 (m, 1H), 8.20 (d, J=8.4 Hz, 1H), 8.48 (s, 1H); HR-MS (FAB) m/z calcd. for $C_{47}H_{39}N_4O_{10}S$ 851.2387, found 851.2382 $[M+H]^+$.

Preparation Example 5

1-O-trityl-2,3,4,5-tetra-O—(N-{bis-[3-(N',N''-bis-(tert-butoxycarbonyl)-guanidino)-propyl]}-6-amino-hexanoyl)-D-sorbitol (5)

A cationic compound of which a backbone is sorbitol and which has eight guanidine groups was prepared with reference to the method described in Example 1 of Korean Patent No. 10-0699279. Specifically, sorbitol having a protecting group was prepared from D-glucose protected as in Preparation Example 1 described in Korean Patent No. 10-0699279, and the aminocaproic acid derivative having N,N'-di-Boc-guanidine group prepared as in Preparation Example 6 was used to prepare a compound having eight guanidine groups as in Example 1.

Preparation Example 6

1-O—[N-(tert-butoxycarbonyl)-6-aminohexanoyl]-2,3,4,5-tetra-O—(N-{bis-[3-(N',N''-bis-(tert-butoxy-carbonyl)-guanidino)-propyl]}-6-aminohexanoyl)-6-O-trityl-D-sorbitol (6)

The compound (5) (250 mg, 0.076 mmol) of Preparation Example 5 was dissolved in anhydrous $CH_2Cl_2$ (20 ml) with 6-tert-butoxycarbonyl-aminohexanoic acid (35.4 mg, 0.152 mmol), EDC (29 mg, 0.152 mmol), and DMAP (2 mg, 0.015 mmol). The reaction mixture was stirred at room temperature under $N_2$ atmosphere for 2 days. Distilled water was added to terminate the reaction, and the solution was extracted with $CH_2Cl_2$. The extract was washed with a saturated $NaHCO_3$ solution and then washed with brine. Then, the resultant was dried over anhydrous $Na_2SO_4$. The organic phase was concentrated in vacuo, and the residue was purified by $SiO_2$ column chromatography to give the title compound (6) (250 mg, 93%).

$^1$H NMR ($CDCl_3$): δ 1.51-1.77 (m, 191H), 2.28-2.35 (m, 10H), 2.54-2.61 (m, 24H), 3.08-3.11 (m, 2H), 3.43 (br s, 16H), 3.60-4.41 (m, 4H), 4.81-5.62 (m, 4H), 7.24-7.42 (m, 15H), 8.51 (s, 8H), 11.5 (s, 8H); MALDI-TOF-MS: m/z calcd. for $C_{172}H_{292}N_{29}O_{45}$ 3484.14, found 3484.23 $[M+H]^+$.

Preparation Example 7

1-O—[N-(tert-butoxycarbonyl)-6-aminohexanoyl]-2,3,4,5-tetra-O—(N-{bis-[3-(N',N''-bis-(tert-butoxy-carbonyl)-guanidino)-propyl]}-6-aminohexanoyl)-D-sorbitol (7)

A flash silica gel column was packed in hexane containing 1% Et3N on the bottom, and then hexane containing 1% TFA at the top. Then, a sea sand layer was placed therebetween. The compound (6) (240 mg, 0.068 mmol) prepared in Preparation Example 6 was dissolved in $CH_2Cl_2$. The solution was loaded on the column and eluted with increasing concentration of MeOH in $CH_2Cl_2$, to give the title compound (7) (120 mg, 54%) as a colorless foamy solid.

$^1$H NMR ($CDCl_3$): δ 1.26-1.69 (m, 175H), 1.91-2.04 (m, 16H), 2.33 (br s, 10H), 2.86-3.22 (m, 26H), 3.47 (br s, 16H), 3.70-4.51 (m, 4H), 4.65-5.53 (m, 4H), 8.51 (s, 8H), 11.45 (s,

8H); $^{13}$C NMR (CDCl$_3$): δ 24.4, 26.2, 27.9, 28.2, 33.8, 38.5, 40.3, 50.4, 53.1, 79.2, 83.2, 153.0, 156.5, 163.3, 170.5, 172.5, 172.7; MALDI-TOF-MS: m/z calcd. for C$_{153}$H$_{278}$N$_{29}$O$_{45}$ 3242.03, found 3242.15 [M+H]$^+$.

Preparation Example 8

1-O-[20-O—(N-succinyl-6-aminohexanoyl)camp-tothecin]-2,3,4,5-tetra-O—(N-{bis-[3-(N',N''-bis-(tert-butoxycarbonyl)-guanidino)-propyl]}-6-amino-hexanoyl)-6-O—[N-(tert-butoxycarbonyl)-6-aminohexanoyl]-D-sorbitol (8)

The compound (7) (100 mg, 0.030 mmol) prepared in Preparation Example 7 was dissolved in anhydrous CH$_2$Cl$_2$ (20 ml) with the compound (3) of Preparation Example 3 (34 mg, 0.060 mmol), EDC (11.5 mg, 0.060 mmol), and DMAP (1.0 mg, 0.006 mmol). The reaction mixture was stirred at room temperature under N$_2$ atmosphere for 2 days. Distilled water was added to the mixture, and then the solution was extracted with CH$_2$Cl$_2$. The extract was washed with a saturated NaHCO$_3$ solution, and then washed with brine. Then, the resultant was dried over anhydrous Na$_2$SO$_4$. The organic layer was concentrated in vacuo, and the residue was purified by SiO$_2$ column chromatography to give the title compound (8) (60 mg, 52%).
$^1$H NMR (CDCl$_3$): δ 0.98 (t, J=7.2 Hz, 3H), 1.25-1.77 (m, 197H), 2.00-2.84 (m, 42H), 3.08-3.20 (m, 4H), 3.44-3.46 (m, 16H), 3.65-4.5 (m, 4H), 4.87-5.70 (m, 8H), 7.21 (s, 1H), 7.67 (t, J=7.8 Hz, 1H), 7.84 (t, J=7.8 Hz, 1H), 7.95 (d, J=8.4 Hz, 1H), 8.21 (d, J=8.4 Hz, 1H), 8.42 (s, 1H), 8.50 (s, 8H), 11.47 (s, 8H); $^{13}$C NMR (CDCl$_3$): δ 8.7, 21.3, 24.7, 25.9, 27.1, 28.2, 28.5, 31.9, 33.7, 34.0, 39.3, 45.9, 50.1, 51.4, 52.9, 53.6, 53.7, 67.2, 79.3, 83.1, 96.1, 128.2, 128.4, 128.7, 129.6, 130.9, 131.5, 146.1, 146.4, 149.0, 152.5, 153.2, 156.3, 157.5, 163.7, 172.8; MALDI-TOF-MS: m/z calcd. for C$_{183}$H$_{307}$N$_{32}$O$_{52}$ 3785.23, found 3785.29 [M+H]$^+$.

Preparation Example 9

1-O-[20-O—(N-succinyl-6-aminohexanoyl)camp-tothecin]-2,3,4,5-tetra-O—(N-{bis-[3-(N',N''-bis-(tert-butoxycarbonyl)-guanidino)-propyl]}-6-amino-hexanoyl)-6-O-(6-aminohexanoyl)-D-sorbitol•9HCl (9)

The compound (8) (60 mg, 0.016 mmol) prepared in Preparation Example 8 was stirred, with ethyl acetate (10 ml) saturated with HCl (g), in vacuo at room temperature for 2 days. The resulting precipitate was washed three or more times with hexane and dried in vacuo. The resultant was dissolved in distilled water, filtered through a polytetrafluoroethylene (PTFE) syringe filter, and then lyophilized to give a crude product. The crude product was purified by preparative RP-HPLC (GRACEVYDAC, C-18) (2.0 ml min$^{-1}$, 10:90=CH$_3$CN:H$_2$O, 220 nm), to give the title compound (9) (HCl salt) (35 mg, 92%) as a white foamy solid.
$^1$H NMR (D$_2$O+MeOD): δ 1.08 (t, J=7.2 Hz, 3H), 1.27-1.42 (m, 12H), 1.67-1.69 (m, 22H), 2.05-2.08 (m, 14H), 2.26-2.54 (m, 14H), 2.72 (m, 2H), 3.01 (m, 2H), 3.25-3.33 (m, 46H), 3.57 (m, 2H), 4.01-4.52 (m, 4H), 4.53-5.70 (m, 8H), 6.75-8.41 (m, 6H); $^{13}$C NMR (D$_2$O+MeOD): δ 8.5, 23.9, 24.4, 25.1, 26.7, 27.1, 27.9, 29.5, 30.7, 31.5, 32.1, 33.3, 34.7, 39.7, 40.5, 40.7, 51.7, 54.5, 55.4, 68.2, 77.9, 99.0, 120.1, 129.1, 129.6, 132.7, 134.1, 149.1, 152.5, 154.5, 158.3, 159.2, 171.6, 176.1; MALDI-TOF-MS: m/z calcd. for C$_{98}$H$_{171}$N$_{32}$O$_{18}$ 2084.34, found 2084.39 [M+H]$^+$; analytical HPLC (GRACEVYDAC C-18): tR=2.72 min (flow rate=1 ml min$^{-1}$, UV 220 nm, CH$_3$CN:H$_2$O=70:30).

Preparation Example 10

1-O-[20-O—(N-succinyl-6-aminohexanoyl)camp-tothecin]-2,3,4,5-tetra-O—(N-{bis-[3-N',N''-bis-(tert-butoxycarbonyl)-guanidino)-propyl]}-6-amino-hexanoyl)-6-O-[6-(fluoresceinyl-5-thioureido)-hexanoyl]-D-sorbitol•8HCl (10)

To a solution of the compound (9) prepared in Preparation Example 9 (10 mg, 0.004 mmol) in DMF (2 mL), diisopropylethylamine (0.015 ml, 0.083 mmol) and fluorescein-5-isothiocyanate (2 mg, 0.005 mmol) were added at room temperature. After performing stirring for 24 hours in the dark, the solution was repeatedly concentrated at 45° C. under reduced pressure by azeotropic removal with toluene. The residue was dissolved in MeOH and filtered through a polytetrafluoroethylene (PTFE) syringe filter. The resulting solution was evaporated. The crude product was successively purified by MPLC (C8 column) and preparative RP-HPLC (GRACEVYDAC, MONOMER C-18) (2.0 ml min$^{-1}$, 10% CH$_3$CN in H$_2$O, 220 nm), to give the title compound (10) as a sticky orange solid (6 mg, 52%).
$^1$H NMR (MeOD): δ 1.04 (t, J=7.2 Hz), 1.38-1.42 (m, 12H), 1.69 (m, 22H), 2.01-2.04 (m, 14H), 2.39-2.69 (m, 16H), 3.07-3.13 (m, 50H), 3.72-4.51 (m, 4H), 4.54-5.65 (m, 8H), 6.61-6.65 (m, 2H), 6.70 (s, 2H), 6.83-6.87 (m, 2H), 7.20 (d, J=7.2 Hz, 1H), 7.38 (s, 1H), 7.71-7.76 (m, 2H), 7.87 (t, J=8.1 Hz, 1H), 8.10 (d, J=8.7 Hz, 1H), 8.18 (d, J=9.0 Hz, 1H), 8.32 (m, 1H), 8.69 (s, 1H); $^{13}$C NMR (MeOD): δ 8.6, 25.6, 25.9, 27.8, 30.0, 30.4, 32.2, 32.6, 35.1, 37.2, 40.4, 44.0, 52.2, 54.9, 68.3, 98.3, 104.2, 120.1, 129.7, 130.3, 131.4, 132.5, 149.3, 159.2, 174.2; MALDI-TOF-MS: m/z calcd. for C$_{19}$H$_{181}$N$_{33}$O$_{23}$S 2472.37, found 2472.51[M]$^+$; analytical HPLC (GRACEVYDAC C-18): tR=2.30 min (flow rate=1 ml min$^{-1}$, UV 220 nm, CH$_3$CN:H$_2$O=70:30), purity 98+%.

Example 1

Synthesis of Linker- or Fluorescein-Bound Camptothecin

[Scheme 1]

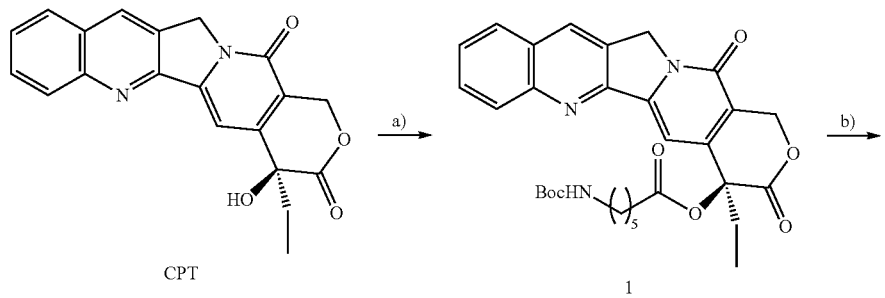

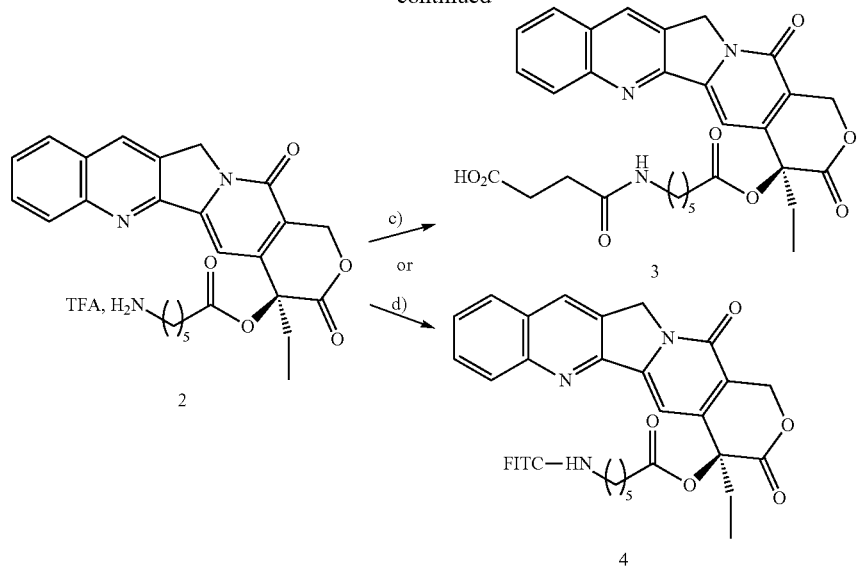

A method of binding a linker or fluorescein to camptothecin is shown in Scheme 1 above. First, a CPT derivative having a linker was synthesized. The hydroxyl group of CPT was bound to Boc-aminohexanoic acid in the presence of EDC and DMAP, to give compound (1). Then, the Boc protecting group was removed with 10% TFA in CH$_2$Cl$_2$ to give compound (2) which did not require further purification. The compound (2) was treated with succinic anhydride, DMAP, and pyridine in DMF, to give compound (3) which was used as a precursor of the CPT-bound compound. In order to compare the delivery efficiency between the CPT-bound compound of Example 2 and a blank compound (that is, CPT to which only FITC is bound), the compound (2) was treated with FITC-1 and triethylamine in DMF, to give compound (4) which is a blank compound into which fluorescein is incorporated via isothiocyanate linkage (Scheme 1).

Example 2

Synthesis of CPT-Bound Compound

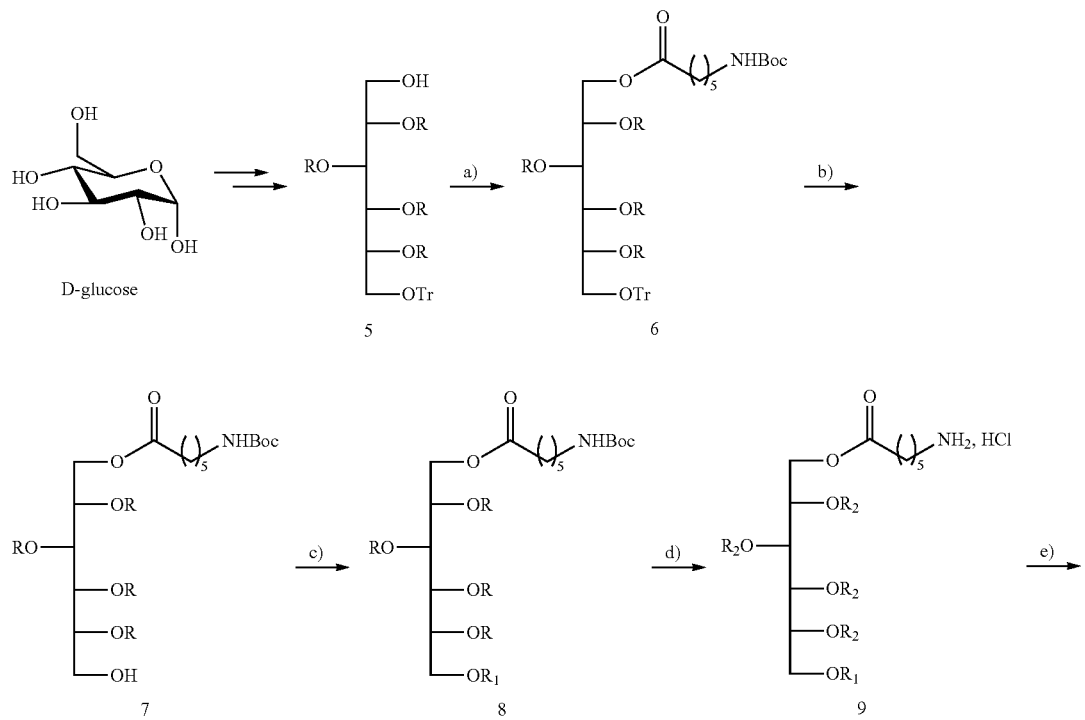

-continued

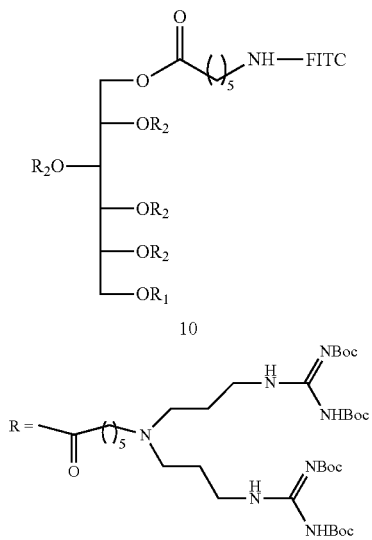

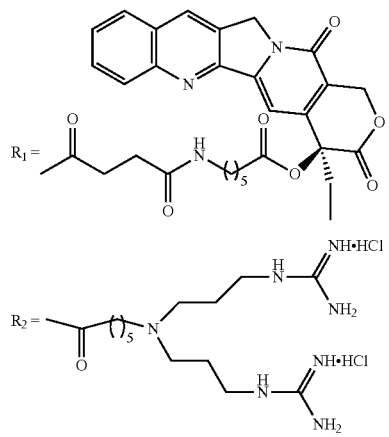

A CPT-bound compound was synthesized by designing the compound so that a plurality of guanidines are bound via linkers to ends of a monosaccharide-based compound, a fluorescent probe is bound to one end thereof for microscopic analysis, and CPT is held as a cargo at the other end thereof.

For the monosaccharide α-D-glucose was reduced to a linear structure to form sorbitol, a reduced monosaccharide. The sorbitol was tritylated and acylated to form compound (5). The compound (5) has Boc-protected bis-guanidine and four branched side chains, thereby giving a total of eight Boc-protected guanidines.

For attachment of a fluorescent probe, Boc-aminohexanoic acid which is used as a linker was bound to the compound (5) by being stirred with EDC and DMAP in DMF, to give compound (6). The trityl group in the compound (6) was selectively removed in the presence of a plurality of Boc groups using an elution gradient of a $CH_2Cl_2$/MeOH mixture through a flash $SiO_2$ column packed in hexane containing 1% TFA at the top and hexane containing 1% Et3N on the bottom. The resulting compound (7) was combined with the compound (3) which is a CPT derivative, by being stirred with EDC and DMAP in DMF, to give compound (8) in suitable yield. The CPT and the linker were covalently bound to each other by ester bonding, whereby the compound (8) can be hydrolyzed after cell uptake to release a payload.

All Boc groups of the compound (8) were removed with ethyl acetate saturated with HCl, to prepare compound (9) which was purified by preparative HPLC. This resulted in conversion of all guanidine residues into guanidinium chloride salts, which showed high solubility in aqueous solutions. The compound (9), a CPT-bound compound, was used as a model substrate for biological analysis. In addition, for attachment of a fluorescent probe, the compound (9) was treated with FITC-I and DIPEA in DMF, to give compound (10) to which a fluorescent probe is attached. The crude product was purified by MPLC with a C-8 reversed phase column and repurified by preparative HPLC, to give compound (10) with a purity of 98% or higher (Scheme 2).

Experimental Example 1

Cell Culture

High glucose Dulbecco's modified Eagle's medium (DMEM), Roswell Park Memorial Institute (RPMI) 1640, Dulbecco's phosphate buffered saline, pH 7.4 (DPBS), fetal bovine serum (FBS), and trypsin/EDTA were obtained from Gibco™ and Thermo Fischer Scientific. Mitotracker and Lysotracker were obtained from Invitrogen Inc. (USA). 3-(4,5-Dimethyl-2-thiazolyl)-2,5-diphenyl-2H-tetrazolium bromide (MTT) was purchased from Sigma-Aldrich Korea Ltd. All solutions were prepared using Milli-Q purified water (18.2 Me). HeLa cells were cultured in 10% (v/v) FBS containing DMEM and penicillin at 37° C. under a wet 5% $CO_2$ environment. For SW480 cells and HT-29 cells, RMPI 1640 medium was used.

Experimental Example 2

Identification of Cell Uptake

Cell uptake effects on whether the CPT-bound compound of Example 2 (compound (10)) and the compound (4) (CPT to which only FITC is bound) can be translocated into a cell through the cell membrane were compared using a confocal microscope.

HeLa cells ($1\times10^5$ cells per well) were seeded in a 35 mm cover glass bottom dish (SPL Life Sciences Co., Ltd., Korea) and incubated for 24 hours. The cells were washed with PBS ($\times1$), and then treated with 2 ml of serum-free DMEM (1% v/v DMSO) containing 10 M compound (4) or compound (10), respectively. After incubation at 37° C. for 30 minutes, the cells were washed three times with cold PBS to remove non-internalized samples. Live HeLa cells were examined with a confocal laser scanning microscope (Olympus Fluoview FV1000) equipped with an oil immersion lens (NA 1.30, 40×). FITC was excited at 488 nm with an argon laser and fluorescence was observed with a 500 to 530 nm emission band filter. Mitotracker and Lysotracker were excited at 543 mm with HeNe laser and fluorescence was observed with a 600 to 700 nm emission filter. Each analysis was repeated three times.

Cell uptake in live cells was visually checked through labeled fluorescence. As a result, it was identified that a strong green fluorescence appears mainly in the cytoplasm of cells treated with the compound (10). From this, it was found that the compound (10) can penetrate the cell membrane and diffuse into the cytoplasm. However, unlike the compound (10), intracellular fluorescence was not observed in the compound (4). As a result, it was found that the compound (10) can effectively deliver CPT into a cell, and that a plurality of guanidines in the CPT-bound compound are essential for imparting cell membrane permeability. In addition, it was found that the compound (10) can enter a cell through passive diffusion or endocytosis (FIG. 1).

Experimental Example 3

Identification of Intracellular Localization

HeLa cells were stained simultaneously with the compound (10) and specific organelle markers (Mitotracker and Lysotracker). Live HeLa cells were treated with the compound (10) (10 uM) for the first 30 minutes, and then treated with Mitotracker (100 nM, Invitrogen), a mitochondrial marker, for 30 minutes. Co-localization was markedly observed in both the compound (10) and Mitotracker fluorescence (a in FIG. 2), and it was found that the compound (10) has a high affinity for mitochondria.

Figure 2:
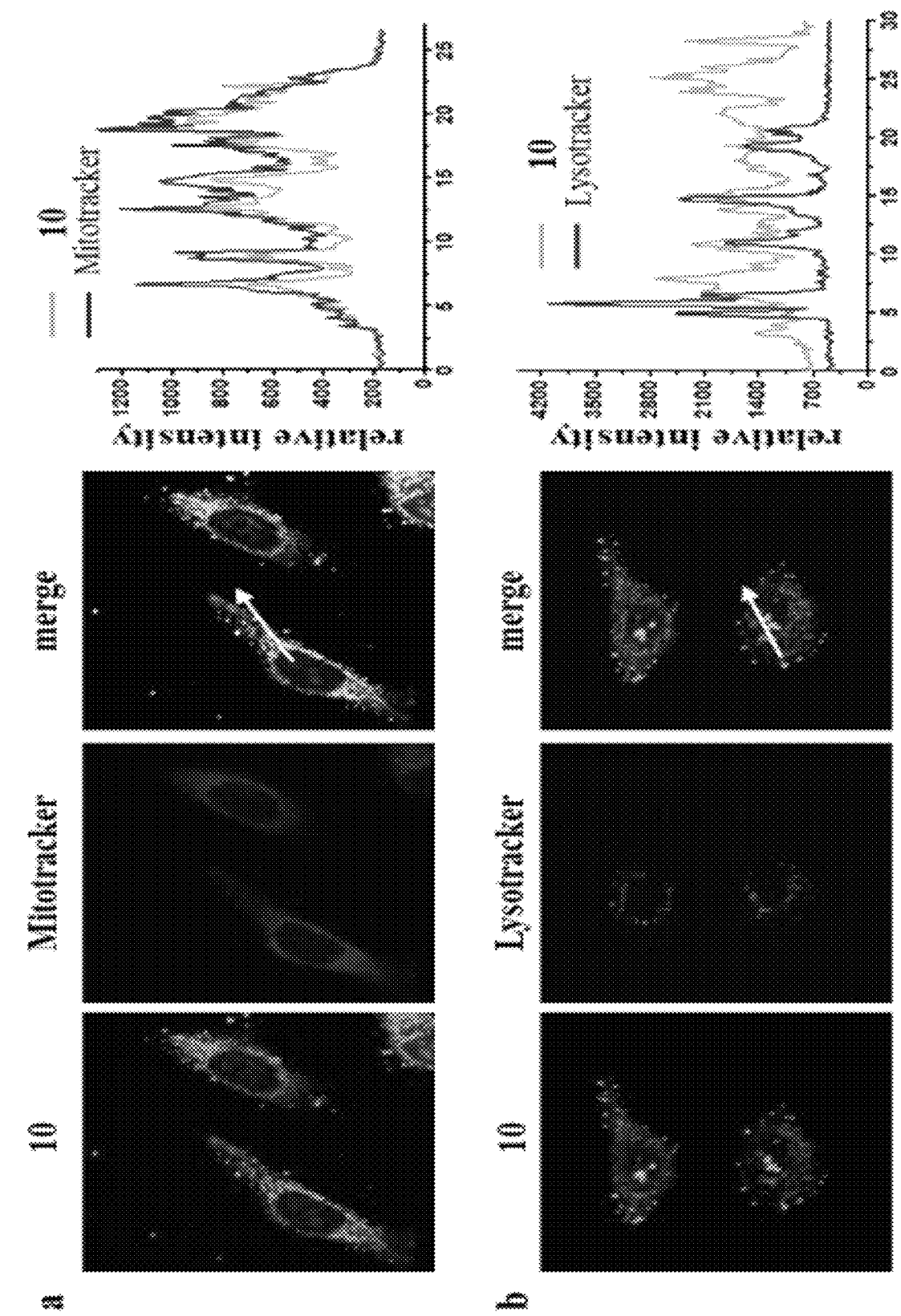
FIG. 2 illustrates results obtained by identifying the degree of intracellular localization of a CPT-bound compound according to an embodiment.

In contrast, in a case where the HeLa cells are treated with Lysotracker (200 nM, Invitrogen), a lysosomal marker, co-localization was not observed (b in FIG. 2). The intensity of each fluorescence signal is indicated by an arrow to show a degree of co-localization (right side in FIG. 2).

In addition, intracellular localization was checked by treatment with 10 μM compound (10). As a result, it was identified that the compound shows intracellular localization for mitochondria. On the other hand, confocal microscopy images obtained in a case where 20 μM compound (10) is incubated with the HeLa cells for 30 minutes were checked. As a result, it was found that fluorescence exists even inside the nucleus. From this, it was found that the CPT-bound compound may exist inside the nucleus in a case of being at a specific concentration or higher. This shows that the CPT-bound compound can reach an inside of the nucleus, thereby achieving a desired drug effect of CPT.

Experimental Example 4

Identification of Tissue Biodistribution

Figure 3:
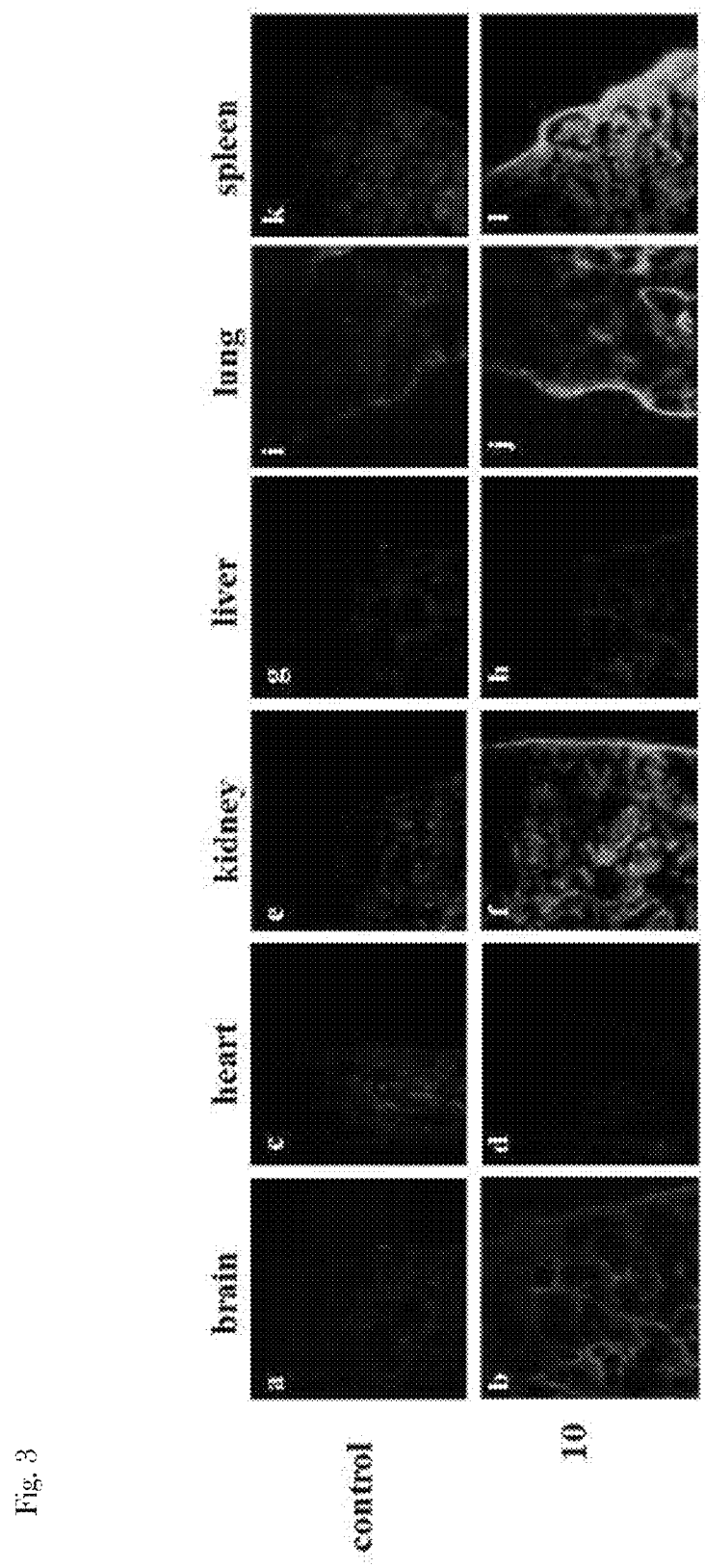
FIG. 3 illustrates results obtained by identifying the degree of tissue biodistribution of a CPT-bound compound according to an embodiment. Here, the exposure time was set to be 9,000 ms in a and b, 2,000 ms in c and d, 2500 ms in e and f, 2,000 ms in g and h, 7,000 ms in i and j, and 1500 ms ink and 1.

In a case where the compound (10), a CPT-bound compound, is intraperitoneally injected (ip), tissue distribution in mice was observed. The compound (10) (HCl salt, 93.4 mg $kg^{-1}$) was dissolved in sterile water and injected into 8 week old mice (C57BL/6). After 30 minutes, the mice were perfused with paraformaldehyde (4%) in PBS (pH 7.4). The major organs (brain, heart, kidney, liver, lung, and spleen) were collected and incubated overnight in a sucrose solution (0.5 M in PBS). The tissue was frozen in a cryoprotectant and cut into 15 m sections. After drying, each section was transferred to a glass slide and treated with Triton X-100 for 15 minutes. Observations were made through a fluorescence microscope (Axioplan 2). As a result, it was shown that the CPT-bound compound is observed mainly in the kidney, the lung, the spleen, and is also observed even in the brain (FIG. 3).

Experimental Example 5

Measurement of Cytotoxicity

Cytotoxicity of a CPT-bound compound (compound (9)) was compared with that of CPT alone through MTT assay. Here, the compound (9), which is a CPT-bound compound containing no FITC, was used to prevent unnecessary effects which may be induced by a fluorescent probe.

SW480 cells and HT-29 cells ($4.5\times10^3$ cells per well) were seeded in a 96-well plate. After 24 hours, the medium was replaced with serum-free RMPT 1640. After an additional 24 hours, the cells were treated with the compound (9) or CPT, respectively, at different concentrations (1.28 nM, 6.4 nM, 32 nM, 0.16 M, 0.8 M, 4 M, 20 M, 100 M). The treated cells were incubated for 48 hours, washed with cold PBS, and then exposed to MTT in the medium for 4 hours. The medium was replaced with DMSO, and the dissolved formazan dye was quantified by measuring the absorbance at 500 nm. Non-treated cells were measured in the same manner as a control.

Figure 4:
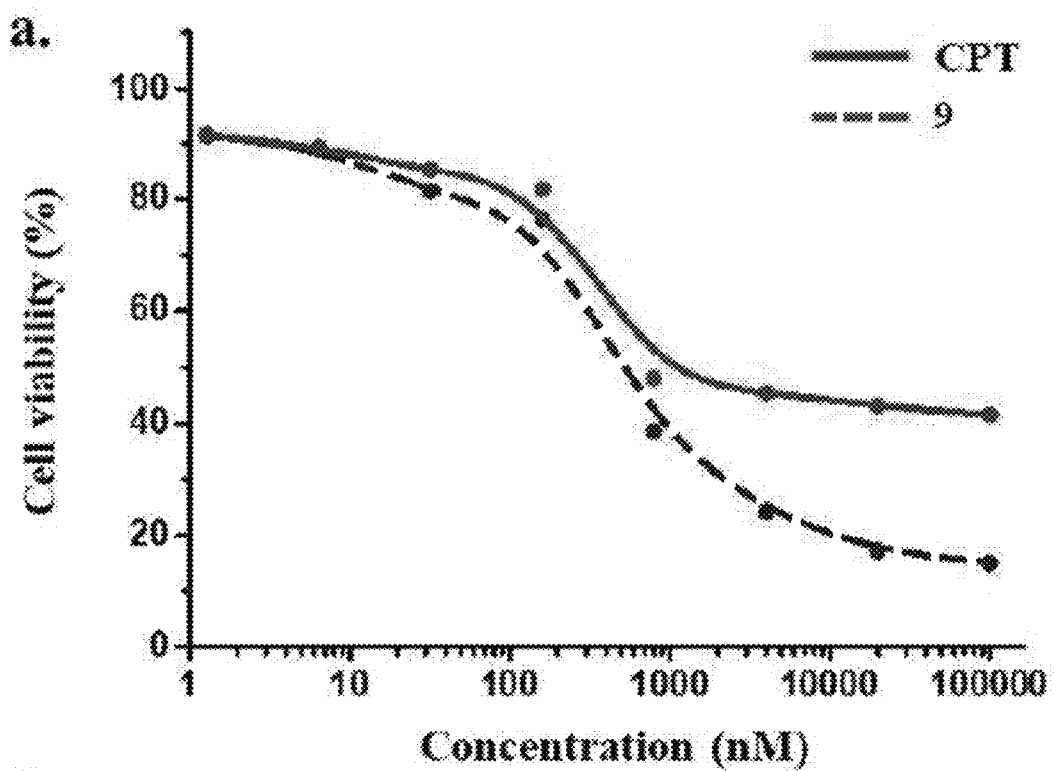
FIG. 4 illustrates results obtained by comparing cytotoxicity of a CPT-bound compound according to an embodiment with that of CPT alone. Here, a represents cytotoxicity results in SW480 cells, and b represents cytotoxicity results in HT-29 cells.
Figure 4:
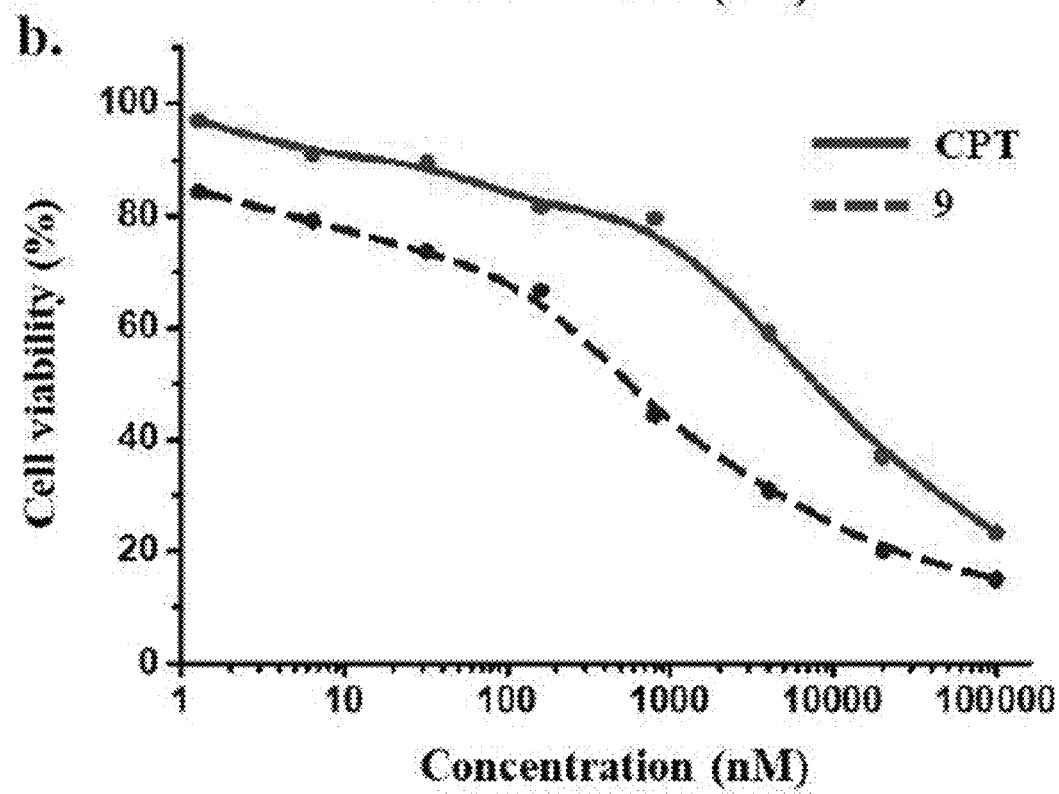
Figure 5:
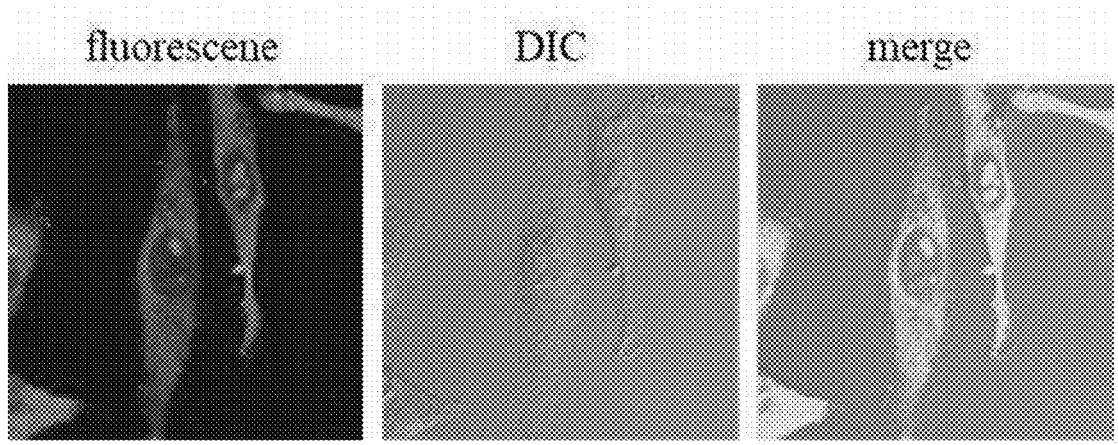
FIG. 5 illustrates results obtained by identifying the degree of intracellular localization of a CPT-bound compound according to an embodiment.

As a result, it was found that the compound (9) decreases cell viability as compared with CPT, thereby exhibiting much better drug efficacy against a colorectal cancer cell line. $IC_{50}$ values of CPT and the compound (9) in SW480 cells were 1.53 M and 0.54 M, respectively, while $IC_{50}$ values thereof in HT-29 cells were 0.99 M and 0.57 M, respectively. From the above results, it was found that the compound (9) can penetrate into cells in an efficient manner as compared with CPT alone, thereby exhibiting enhanced intracellular drug efficacy (FIG. 4).

In order to improve the drug delivery problem of CPT known to have an anticancer effect, CPT-bound compounds containing eight guanidines essential for cell internalization were designed and synthesized (compounds (9) and (10)). As a result, it was found through a confocal microscope that the CPT-bound compounds are rapidly internalized into HeLa cells and target mitochondria. It was shown that such compounds exhibit specificity toward the kidney, the lung, and the spleen. In addition, cytotoxicity of the CPT-bound compounds was quantified by MTT assay. As a result, it was found that the CPT-bound compounds exhibit much lower $IC_{50}$ values than CPT in SW480 cells and HT-29 cells, indicating that drug efficacy of the CPT-bound compounds is maintained well even after cell internalization into cells.

The invention claimed is:

1. A camptothecin (CPT)-bound compound or a pharmaceutically acceptable salt thereof, wherein the CPT-bound compound is represented by the following Formula 1:

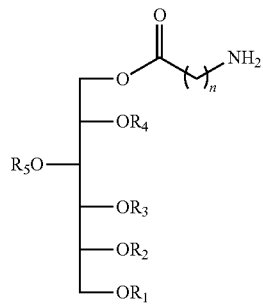

[Formula 1]

wherein $R_1$ to $R_5$ are each CPT, a CPT derivative, -linker1-CPT, -linker1-CPT derivative, guanidine, or -linker2-guanidine; and wherein three or more of $R_1$ to $R_5$ are guanidine or -linker2-guanidine.

2. The CPT-bound compound or a pharmaceutically acceptable salt thereof of claim 1, wherein the monosaccharide is any one selected from the group consisting of glucose, sorbitol, fructose, mannose, galactose, and ribose.

3. The CPT-bound compound or a pharmaceutically acceptable salt thereof of claim 1, wherein the CPT derivative is selected from the group consisting of topotecan, irinotecan, silatecan, cositecan, exatecan, lutotecan, gimatecan, belotecan, rubitecan, and a combination thereof.

4. The CPT-bound compound or a pharmaceutically acceptable salt thereof of claim 1, wherein the linker1 is represented by the following formula:

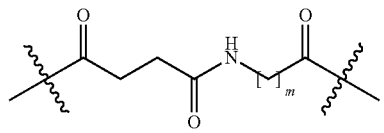

wherein m is an integer of 3 to 8.

5. The CPT-bound compound or a pharmaceutically acceptable salt thereof of claim 1, wherein the linker2 is represented by the following formula:

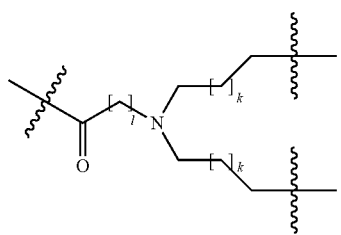

wherein l and k are each an integer of 3 to 8.

6. The CPT-bound compound or a pharmaceutically acceptable salt thereof of claim 1, wherein

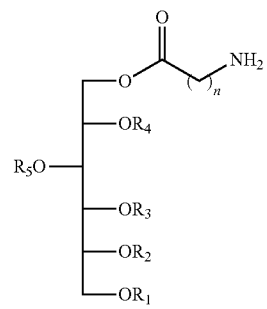

$R_1$ is represented by the following Formula 2,

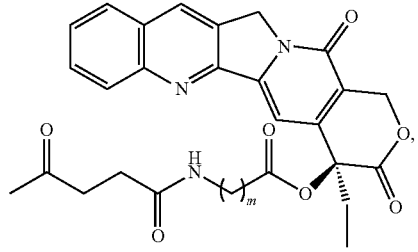

[Formula 2]

and
$R_2$ to $R_5$ are each represented by the following Formula 3,

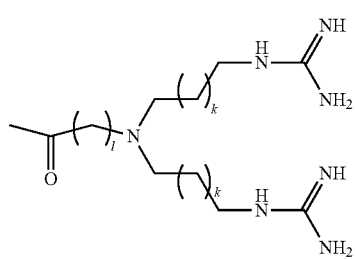

[Formula 3]

in the formulae, n, m, l, and k are each an integer of 3 to 8.

7. The CPT-bound compound or a pharmaceutically acceptable salt thereof of claim 1, wherein the CPT-bound compound is 1-O-[20-O—(N-succinyl-6-aminohexanoyl) camptothecin]-2,3,4,5-tetra-O—(N-{bis-[3-(N',N''-bis-(tert-butoxycarbonyl)-guanidino)-propyl]}-6-aminohexanoyl)-6-O-(6-aminohexanoyl)-D-sorbitol.

8. The CPT-bound compound or a pharmaceutically acceptable salt thereof of claim 1, wherein the pharmaceutically acceptable salt of the CPT-bound compound is in form of an acid addition salt formed with any one inorganic acid selected from the group consisting of hydrochloric acid, sulfuric acid, phosphoric acid, nitric acid, and hydrobromic acid.

9. The CPT-bound compound or a pharmaceutically acceptable salt thereof of claim 8, wherein the pharmaceutically acceptable salt of the CPT-bound compound is 1-O-[20-O—(N-succinyl-6-aminohexanoyl)camptothecin]-2,3,4,5-tetra-O—(N-{bis-[3-(N',N"-bis-(tert-butoxycarbonyl)-guanidino)-propyl]}-6-aminohexanoyl)-6-O-(6-aminohexanoyl)-D-sorbitol. 8HCl; or 1-O-[20-O—(N-succinyl-6-aminohexanoyl)camptothecin]-2,3,4,5-tetra-O—(N-{bis-[3-(N',N"-bis-(tert-butoxycarbonyl)-guanidino)-propyl]}-6-aminohexanoyl)-6-O-(6-aminohexanoyl)-D-sorbitol.9HCl.

10. The CPT-bound compound or a pharmaceutically acceptable salt thereof of claim 1, wherein the CPT-bound compound or a pharmaceutically acceptable salt thereof comprises an enantiomer, diastereomer, or a mixture thereof.

11. A pharmaceutical composition comprising as an active ingredient, the CPT-bound compound or a pharmaceutically acceptable salt thereof of claim 1.

\* \* \* \* \*